(12) United States Patent
Couves et al.

(10) Patent No.: US 7,223,897 B2
(45) Date of Patent: May 29, 2007

(54) PROCESS FOR THE PRODUCTION OF OLEFINS

(75) Inventors: John William Couves, Bourne End (GB); David Charles Griffiths, Esher (GB); Brian Edward Messenger, Englefield Green (GB); Ian Allan Beattie Reid, Southfields (GB)

(73) Assignee: Ineos Europe Limited, Hampshire (GB)

(*) Notice: Subject to any disclaimer, the term of this patent is extended or adjusted under 35 U.S.C. 154(b) by 0 days.

(21) Appl. No.: 11/256,194

(22) Filed: Oct. 24, 2005

(65) Prior Publication Data

US 2006/0074268 A1   Apr. 6, 2006

Related U.S. Application Data

(63) Continuation of application No. 10/168,480, filed on Sep. 19, 2002, now abandoned.

(51) Int. Cl.
*C07C 4/02* (2006.01)
*C07C 4/06* (2006.01)

(52) U.S. Cl. ............... 585/650; 585/651; 585/652; 585/654; 585/658; 585/660; 585/661; 585/662; 585/653

(58) Field of Classification Search ............... 585/650, 585/651, 652, 654, 658, 660, 661, 662, 653, 585/663
See application file for complete search history.

(56) References Cited

U.S. PATENT DOCUMENTS

| 3,123,574 | A | 3/1964 | Zajcew |
| 3,437,703 | A | 4/1969 | Reitmeier et al. |
| 3,670,044 | A | 6/1972 | Drehman et al. |
| 4,638,085 | A | 1/1987 | Broecker et al. |
| 4,788,371 | A | 11/1988 | Imai et al. |
| 6,166,283 | A | 12/2000 | Bharadwaj et al. ......... 585/658 |

FOREIGN PATENT DOCUMENTS

| EP | 0 471 320 | 2/1992 |
| EP | 0 478 144 | 4/1992 |
| EP | 0 602 864 | 6/1994 |
| FR | 2 285 340 | 4/1976 |
| JP | 9-221452 | 8/1997 |
| JP | 9-255626 | 9/1997 |
| WO | WO 94/04632 | 3/1994 |
| WO | WO 94/29021 | 12/1994 |
| WO | WO 00/14037 | 3/2000 |

OTHER PUBLICATIONS

Patent Abstracts of Japan, vol. 1998, No. 01, Jan. 30, 1998, JP 09 255626, Sep. 30, 1997.
Patent Abstracts of Japan, vol. 1997, No. 12, Dec. 25, 1997, JP 09 221452, Aug. 26, 1997.
Huff, M., et al; "Ethylene Formation by Oxidative Dehydrogenation of Ethane over Monoliths at Very Short Contact Times"; *J. Phys. Chem.*; vol. 97, pp. 11815-11822 (1993).

*Primary Examiner*—Elizabeth D. Wood
(74) *Attorney, Agent, or Firm*—Nixon & Vanderhye

(57) ABSTRACT

A process for the production of an olefin from a hydrocarbon by autothermal cracking, which process comprises: partially combusting the hydrocarbon and an oxygen-containing gas in the presence of a catalyst, wherein the stoichiometric ratio of hydrocarbon to oxygen is 5 to 16 times the stoichiometric ratio of hydrocarbon to oxygen required for complete combustion of the hydrocarbon to carbon dioxide and water, characterised in that the catalyst comprises palladium and at least one further metal being a Group IIIA, Group IVA, VA, a transition metal or a lanthanide.

6 Claims, 1 Drawing Sheet

PROCESS FOR THE PRODUCTION OF OLEFINS

CROSS-REFERENCE TO RELATED APPLICATION

This application is a continuation of application Ser. No. 10/168,480, filed Sep. 19, 2002, now abandoned the entire content of which is hereby incorporated by reference in this application.

BACKGROUND OF THE INVENTION

The present invention relates to a process for the production of olefins.

Olefins such as ethylene and propylene may be produced by a variety of processes, including the steam cracking of hydrocarbons or by the dehydrogenation of paraffinic feedstocks. More recently, olefins have been produced by a process known as auto-thermal cracking. In such a process, a hydrocarbon feed is mixed with an oxygen-containing gas and contacted with a catalyst. The hydrocarbon feed is partially combusted, and the heat produced is used to drive the dehydrogenation reaction.

An example of an auto-thermal cracking process is described in EP 0 332 289. The patent describes platinum group metals as being capable of supporting combustion beyond the fuel rich limit of flammability. Preferred catalysts are supported platinum catalysts such as platinum/gamma alumina spheres, and platinum/monoliths such as platinum/cordierite or mullite monoliths.

SUMMARY OF THE INVENTION

In WO 97/26987, such platinum catalysts are modified with Sn or Cu, in the substantial absence of palladium. According to page 4, lines 32 to 34 of the patent, palladium causes the catalyst to coke up and deactivate very quickly.

We have now found that, contrary to prior art suggestions, compositions comprising palladium are effective as catalysts for auto-thermal cracking processes.

Accordingly, the present invention provides a process for the production of an olefin from a hydrocarbon, which process comprises:

partially combusting the hydrocarbon and an oxygen-containing gas in the presence of a catalyst, characterised in that the catalyst comprises palladium and at least one further metal, said further metal being a Group IIIA, Group IVA, VA, a transition metal or a lanthanide.

It should be understood that unless otherwise specified, the term "further metal" covers all elements of Group IIIA, IVA, VA, transition metal and lanthanide series of the Periodic Table.

For the avoidance of doubt, the platinum and at least one further metal in the catalyst may be present in any form, for example, as a metal, or in the form of a metal compound, such as an oxide.

The partial combustion reaction is carried out by contacting a feed comprising the hydrocarbon and a molecular oxygen containing gas with the catalyst. Any suitable oxygen-containing gas may be employed; air being an example.

The preferred stoichiometric ratio of hydrocarbon to oxygen is 5 to 16, preferably, 5 to 13.5 times, more preferably, 6 to 10 times the stoichiometric ratio of hydrocarbon to oxygen required for complete combustion of the hydrocarbon to carbon dioxide and water.

Preferably, hydrogen is co-fed into the reaction. It is believed that in the presence of the catalyst, hydrogen combusts preferentially relative to the hydrocarbon, thereby increasing the olefin selectivity of the overall process.

Additional feed components such as nitrogen, carbon monoxide and steam may also be fed into the reaction.

Suitable Group IIIA metals include Al, Ga, In and Tl. Of these, Ga and In are preferred.

Suitable Group IVA metals include Ge, Sn and Pb. Of these, Ge and Sn are preferred.

Suitable Group VA metals include Sb and Bi. Of these, Bi is preferred.

Suitable metals in the transition metal series are any metal from Group IB to VIIIB of the Periodic Table. In particular, transition metals selected from Groups IB, IIB, VIB, VIIB and VIIIB of the Periodic Table are preferred. Examples of such metals include Cr, Mo, W, Fe, Ru, Os, Co, Rh, Ir, Ni, Pt, Cu, Ag, Au, Zn, Cd and Hg. Preferred transition metals are Mo, Rh, Ru, Ir, Pt, Cu and Zn.

Suitable lanthanides include lanthanum and cerium.

In one embodiment of the present invention, the catalyst comprises only one metal selected from Group IIIA, Group IVA, VA, the transition metal and lanthanide series. For example, the catalyst may comprise palladium and one metal selected from the group consisting of Ga, In, Sn, Ge, Sb, Bi, Cu, Ce and La. Palladium may nominally form between 0.01 and 5.0 wt %, preferably, between 0.01 and 2.0 wt %, and more preferably, between 0.05 and 1.0 wt % of the total weight of the catalyst. It should be noted, however, that not all the metal employed during the preparation of the catalyst necessarily becomes incorporated in the catalyst composition. Thus, the actual loading of metal may differ from the nominal loading. To ensure that the desired actual metal concentrations are achieved, the nominal metal concentrations may have to be varied accordingly.

The actual loading of palladium may be between 10 and up to 100% of the nominal value. Preferably, the actual loadings are above 40%, more preferably, above 70% (e.g. 90 to 99%) of the nominal values. In a preferred embodiment, the actual loading of palladium is between 0.01 and 5.0 wt %, preferably, between 0.01 and 2.0 wt %, and more preferably, between 0.05 and 1.0 wt % of the total weight of the catalyst.

The atomic ratio of palladium to the Group IIIA, IVA VA, transition or lanthanide metal may be 1:0.1–50.0, preferably, 1:0.1–12.0, more preferably, 1:0.2–3.0, and even more preferably, 1:0.5–1.5.

Where the metal is a Group IIIA metal, Ga and In are preferred. Atomic ratios of Pd to Ga or In may be 1:0.1 to 50, preferably, 1:0.1–12.0, and more preferably, 1:0.5–8.0. For example, where the Group IIIA metal is In, the Pd to In ratio may be 1:0.7–2, for example, 1:1.

Where the metal is a Group IVA metal, Sn and Ge are preferred. Sn is most preferred. Atomic ratios of Pd to Sn or Ge may be 1:0.1 to 50, preferably, 1:0.1–12.0, and more preferably, 1:0.5–8.0. For example, the Pd:Ge ratio may be 1:0.1 to 8, preferably, 1:0.5 to 6, for example, 1:5.8; 1:1 and 1:0.5. The Pd:Sn ratio may be 1:0.5 to 17. In one embodiment, the atomic ratio of Pd:Sn is 1:13 to 17, for example 1:15. In another embodiment the atomic ratio of Pd:Sn is 1:0.5 to 4.5, for example 1:2.5.

Where the metal is a Group VA metal, Sb and Bi are preferred. Atomic ratios of Pd to Sb or Bi may be 1:0.1 to 50, preferably, 1:0.1–12.0, and more preferably, 1:0.5–8.0.

Where the metal is a transition metal, the metal is preferably Mo, Rh, Ru, Ir, Zn, and more preferably, Cu. Preferred atomic ratios of Pd:Cu are 1:0.1–3.0, preferably, 1:0.2–2.0, and more preferably, 1:0.5–1.5, for example, 1:0.8.

Where the metal is a lanthanide, the metal is preferably La or Ce.

In another embodiment, the catalyst comprises at least two metals selected from Group IIIA, Group IVA, VA, the transition metal and lanthanide series. For example, the catalyst may comprise Pd, Pt and Cu, or Pd, Pt and Sn. Palladium may nominally form between 0.01 and 5 wt %, preferably, between 0.01 and 2.0 wt %, and more preferably, 0.05–1.0 wt % of the total weight of the catalyst. As described above, the actual loading of metal may differ from the nominal loading. Thus, the actual loading of palladium may be between 10 and up to 100% of the nominal value. Preferably, the actual loadings are above 40%, more preferably, above 70% (eg 90 to 99%) of the nominal values. In a preferred embodiment, the actual loading of palladium is between 0.01 and 5 wt %, preferably, between 0.01 and 2.0 wt %, and more preferably, 0.05–1.0 wt % of the total weight of the catalyst.

Where the catalyst comprises at least two metals selected from Group IIIA, Group IVA, VA, the transition metal and lanthanide series, the catalyst preferably comprises a) palladium, b) a further transition metal and c) a Group IIIA or IVA metal. The transition metal (b) is preferably platinum. The metal c) is, preferably, a Group IVA metal, more preferably, Sn or Ge, and most preferably, Sn. The atomic ratio of palladium to metal (b) (e.g. platinum) may be 1:0.1–10.0, preferably, 1:0.5–8.0, and more preferably 1:1.0–5.0. The atomic ratio of palladium to metal c) may be 1:0.1–60, preferably, 1:0.1:50. Thus, where metal c) is Sn, the atomic Pd:Sn ratio may be 1:0.–60, preferably, 1:0.1–50.0. Atomic Pd: metal c) ratios of 1:0.1–12.0 may also be suitable. For example, where metal c) is Cu, the atomic Pd:Cu ratio is preferably 1:0.1–3.0, more preferably, 1:0.2–2.0, and most preferably, 1:0.5–1.5.

The catalyst may be unsupported. For example, the catalyst may be in the form of a metal gauze. Preferably, however, the catalyst employed in the present process is a supported catalyst. The catalyst may be supported on any suitable support. Ceramic supports are generally preferred, although metal supports may also be employed.

Where ceramic supports are used, the composition of the ceramic support may be any oxide or combination of oxides that is stable at high temperatures of, for example, between 600° C. and 1200° C. The support material preferably has a low thermal expansion co-efficient, and is resistant to phase separation at high temperatures.

Suitable ceramic supports include lithium aluminium silicate (LAS), alumina ($\alpha$-$Al_2O_3$), yttria stabilised zirconia, alumina titanate, niascon, and calcium zirconyl phosphate. The supports may be wash-coated, for example, with $\gamma$-$Al_2O_3$.

The structure of the support material is important, as this may affect flow patterns through the catalyst. Such flow patterns may influence the transport of reactants and products to and from the catalyst surface, thereby affecting the catalyst's activity. Preferably, the substrate is a continuous multi-channel ceramic structure, such as a foam, a regular channelled monolith or a fibrous pad. The pores of foam monolith structures tend to provide tortuous paths for reactants and products. Such supports may have 20 to 80, preferably, 30 to 50 pores per inch. Channel monoliths generally have straighter, channel-like pores. These pores are generally smaller, and there may be 80 or more pores per linear inch of catalyst. The support may be in the form of spheres or other granular shapes, or may be present as a thin layer or wash coat on another substrate.

The catalyst employed in the present invention may comprise further elements, such as alkali metals. Suitable alkali metals include lithium, sodium, potassium and caesium.

The catalyst employed in the present invention may be prepared by any method known in the art. For example, gel methods and wet-impregnation techniques may be employed. Typically, the support is impregnated with one or more solutions comprising the metals, dried and then calcined in air. The support may be impregnated in one or more steps. Preferably, multiple impregnation steps are employed. The support is preferably dried and calcined between each impregnation, and then subjected to a final calcination, preferably, in air. The calcined support may then be reduced, for example, by heat treatment in a hydrogen atmosphere.

In the case of a catalyst comprising palladium; platinum and tin, the support material is preferably impregnated in a palladium/platinum solution, and then in a solution comprising tin. Once impregnated, the catalyst is dried at eg 50 to 200° C., and calcined at eg 100 to 700° C., e.g. 300 to 700 between each impregnation. The support is then subjected to a final calcination step at eg 400 to 1500° C. in air. The catalyst may then be reduced in, for example, a hydrogen atmosphere. This reduction treatment may be carried out at temperatures of up to 1000° C., for example, 100 to 750° C.

The catalyst may be in the form of a fluidised or fixed bed. Preferably, a fixed bed catalyst is employed.

The partial combustion reaction may be suitably carried out at a catalyst exit temperature of between 600° C. and 1200° C., preferably between 850° C. and 1050° C. and most preferably, between 900° C. and 1000° C.

The reaction may be carried out at atmospheric or elevated pressure. Suitable pressures range from 0 to 2 bara, preferably 1.5 to 2 bara, for example 1.8 bara. Elevated pressures of for example, 2 to 50 bara, may also be suitable.

The hydrocarbon may comprise any suitable hydrocarbon. Preferably, gaseous hydrocarbons are employed. Suitable gaseous hydrocarbons include ethane, propane, butane and mixtures thereof.

The hydrocarbon is passed over the catalyst at a gas hourly space velocity of greater than 10,000 $h^{-1}$, preferably above 20,000 $h^{-1}$ and most preferably, greater than 100,000 $h^{-1}$. It will be understood, however, that the optimum gas hourly space time velocity will depend upon the pressure and nature of the feed composition.

Advantageously, heat may also be supplied by pre-heating the hydrocarbon. The temperature to which the hydrocarbon, oxygen-containing gas and (optionally) hydrogen mixture may be preheated, however, is limited by the autoignition properties (eg temperature) of the feed.

Where the cracking reaction is carried out at elevated pressure, the reaction products may be quenched as they emerge from the reaction chamber to avoid further reactions taking place.

Any coke produced in the process of the present invention may be removed by mechanical means, or using one of the decoking methods described in EP 0 709 446.

According to a second aspect of the present invention, there is provided a catalyst comprising a) palladium, b) a further transition metal and c) a metal from Group IIIA, IVA and/or VA.

BRIEF DESCRIPTION OF THE DRAWING

These and other aspects of the present invention will now be described, by way of example, with reference to FIG. 1 of the drawings, which is a schematic view of an apparatus suitable for carrying out an embodiment of the present invention.

DETAILED DESCRIPTION OF PREFERRED EMBODIMENTS

Figure 1:
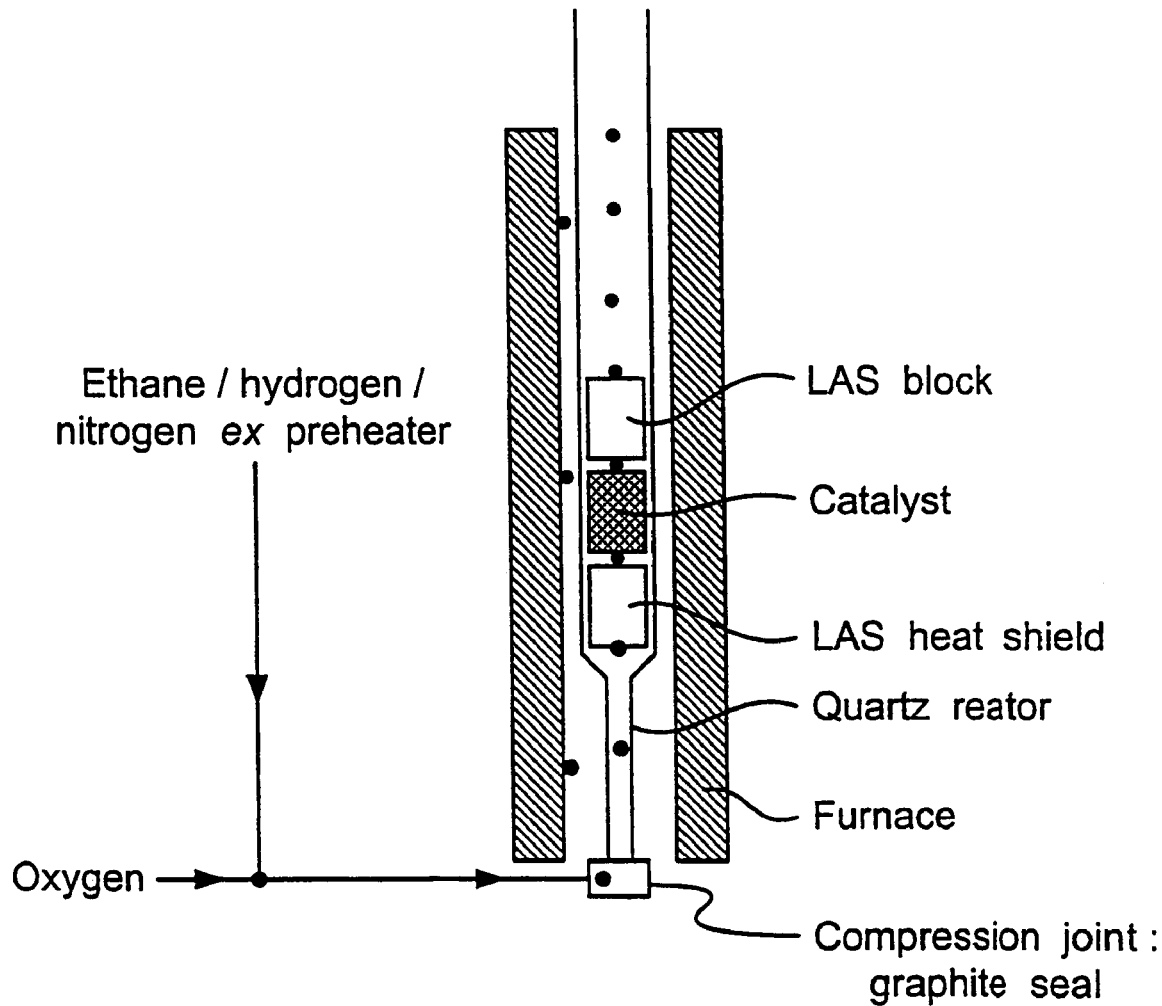

FIG. 1 depicts an apparatus 10 comprising a reactor 12 surrounded by a furnace 14. The reactor 12 may be formed of quartz or metal. Where a metal reactor 12 is employed, the inside of the reactor is lined with quartz (not shown). Typically, metal reactors are more susceptible to heat loss than quartz reactors.

The reactor 12 is coupled to an oxygen supply 16 and a hydrocarbon feed supply 18. The hydrocarbon feed comprises ethane, and small amounts of hydrogen and nitrogen. A catalyst 20 is located within the reactor 12. The catalyst 20 is placed between a pair of LAS heat shields 22, 24.

The furnace is set to minimise heat losses, and the reactants 16, 18, are introduced into the reactor via line 26. As the reactants contact the catalyst 20, some of the ethane in the hydrocarbon feed 18 combusts to produce water and carbon oxides. The hydrogen co-feed also combusts to produce water. Both these combustion reactions are exothermic, and the heat produced is used to drive the dehydrogenation of ethane to ethylene.

EXAMPLES

Example 1

Preparation of Pd/Pt/Sn Catalyst

The catalyst was prepared by multiple impregnation of a lithium aluminium silicate support having a high purity alumina (HPA) wash-coat. The support was impregnated in 1) a platinum/palladium solution (($NH_3$)$_4$Pt$^{II}$Cl$_2$, ($NH_3$)$_4$Pd$^{II}$Cl$_2$), and 2) an SnCl$_2$/HCl solution. Between each impregnation, the support was dried at 120° C., and calcined at 450° C. The catalyst was then calcined in air at 600° C. for 6 hours, and then reduced in an atmosphere of hydrogen (1.0 nl/min), and nitrogen (1.5 nl/min) for 1 hour (at 700° C.).

The catalyst was analysed and found to have 0.36 wt % Pt, 0.04 wt % Pd and 1.85 wt % Sn.

Comparative Example A

1 wt % Pt

A catalyst having a nominal loading of 1 wt % Pt was prepared by impregnating a lithium aluminium silicate support having an HPA wash-coat in a solution of ($NH_3$)$_4$Pt$^{II}$Cl$_2$. The impregnated support was dried at 120° C., and calcined at 450° C. The catalyst was then calcined in air at 1200° C. for 6 hours. The catalyst was analysed and found to have 0.86 wt % Pt.

Comparative Example B

Pt/Sn

A catalyst comprising Pt and Sn was prepared by impregnating a lithium aluminium silicate support having an HPA wash-coat in a solution of 1) ($NH_3$)$_4$Pt$^{II}$Cl$_2$, and 2) SnCl$_2$/HCl. The impregnated support was dried, calcined and reduced as described in connection with Example 1 above. The catalyst was analysed and found to have 0.48 wt % Pt, and 2.80 wt % Sn.

Example 2

The catalysts of Example 1, Comparative Example A and Comparative Example B above were each tested as catalysts for the oxidative dehydrogenation of ethane. Each catalyst was mounted in the apparatus of FIG. 1, and an oxidative dehydrogenation reaction was carried out under the conditions summarised in Table 1 below. For the tests below, a metal reactor 12 was employed.

TABLE 1

|  | 1 (Pd/Pt/Sn) | A (Pt only) | B (Pt/Sn) |
| --- | --- | --- | --- |
| GHSV @ stp/h | 120863 | 119759 | 120268 |
| ethane flow (g/min) | 18.07 | 17.28 | 18.07 |
| hydrogen flow (g/min) | 1.18 | 1.21 | 1.18 |
| Oxygen flow (g/min) | 9.39 | 9.68 | 9.39 |
| nitrogen flow (g/min) | 4.95 | 4.52 | 4.72 |

As shown in Table 2 below, the selectivity of the catalyst of Example 1 towards ethylene is greater than those of Comparative Examples A and B, respectively.

TABLE 2

|  | 1 (Pd/Pt/Sn) | A (Pt only) | B (Pt/Sn) |
| --- | --- | --- | --- |
| ethane conversion (%) | 74.70 | 75.69 | 73.03 |
| selectivity (g ethylene per 100 g ethane converted) | 73.93 | 67.54 | 69.7 |

Example 3

Preparation of 0.2 wt % Pd/4.0 wt % Sn Catalyst

The catalyst was prepared by multiple impregnation of a lithium aluminium silicate support having an HPA wash-coat. The support was impregnated in 1) a palladium solution (($NH_3$)$_4$Pd$^{II}$Cl$_2$), and 2) an SnCl$_2$/HCl solution. Between each impregnation, the support was dried at 120° C., and calcined at 450° C. The catalyst was then calcined in air at 600° C. for 6 hours, and then reduced in an atmosphere of hydrogen (1.0 nl/min), and nitrogen (1.5 nl/min) for 1 hour at 750° C.

The nominal loadings of the resulting catalyst were: 0.2 wt % palladium and 4.0 wt % tin. The catalyst was analysed and found to have 0.19 wt % Pd and 3.18 wt % Sn.

Example 4

Preparation of 1 wt % Pd/4.0 wt % Sn Catalyst

The process of Example 3 was repeated but the concentration of the palladium solution employed was increased such that the nominal loadings of the resulting catalyst were 1 wt % palladium and 4 wt % tin. The catalyst was analysed and found to have 0.98 wt % Pd and 2.70 wt % Sn.

Comparative Example C

A catalyst having the same composition as Comparative Example B was prepared by impregnating a lithium aluminium silicate support having an HPA wash-coat in a solution of 1) $(NH_3)_4Pt^{II}Cl_2$, and 2) $SnCl_2/HCl$. The impregnated support was dried, calcined and reduced as described in connection with Example 1 above. However, instead of being reduced at 700° C., the catalyst of Comparative Example C was reduced at 750° C.

Example 5

The catalysts of Examples 3, 4, and Comparative Examples A and C were each tested as catalysts for the dehydrogenation of ethane. Each catalyst was mounted in the apparatus of FIG. 1, and a dehydrogenation reaction was carried out under the conditions summarised in Table 3 below. For the tests below, a quartz reactor 12 was employed. The quartz reactor employed is less susceptible to heat loss than the metal reactor employed, for example, in Example 2. For this reason, the ethylene selectivities obtained using a quartz reactor tend to be higher than those obtained using a metal reactor.

TABLE 3

|  | 3 (0.2 wt % Pd/4 wt % Sn) | 4 (1 wt % Pd/4 wt % Sn) | A (1 wt % Pt only) | C (1 wt % Pt/4 wt % Sn) |
|---|---|---|---|---|
| GHSV @ stp/h | 120864 | 121073 | 121073 | 120864 |
| ethane flow (g/min) | 18.94 | 18.94 | 18.94 | 18.94 |
| hydrogen flow (g/min) | 1.14 | 1.14 | 1.14 | 1.14 |
| Oxygen flow (g/min) | 9.09 | 9.09 | 9.09 | 9.09 |
| nitrogen flow (g/min) | 4.95 | 5.03 | 5.00 | 4.95 |

As shown in Table 4 below, Examples 3 and 4 are more selective towards ethylene than Comparative Example A. Examples 3 and 4 show a similar selectivity to ethylene as Comparative Example C, but at a higher rate of ethylene conversion.

TABLE 4

|  | 3 (0.2 wt % Pd/4 wt % Sn) | 4 (1 wt % Pd/4 wt % Sn) | A (Pt only) | C (Pt/Sn) |
|---|---|---|---|---|
| ethane conversion (%) | 77.75 | 77.05 | 73.55 | 75.67 |
| selectivity (g ethylene per 100 g ethane converted) | 73.21 | 73.93 | 70.65 | 73.50 |

Example 6

Preparation of Pd/Cu Catalyst

The catalyst was prepared by multiple impregnation of a lithium aluminium silicate support having an HPA wash-coat. The support was calcined in air to 1200° C. for 6 hours prior to impregnation. The support was impregnated in (1) an aqueous palladium solution $(NH_3)_4Pd^{II}Cl_2$ and (2) an aqueous copper solution $Cu(NO_3)_2$. Between each impregnation the support was dried at 120° C. and calcined at 450° C. The catalyst was then calcined at 600° C. for 6 hours then reduced in an atmosphere of hydrogen (1.0 nl/min) and nitrogen 91.5 nl/min) at 750° C. for 1 hour prior to testing.

The target/nominal loadings of the resulting catalyst were 0.2 wt % palladium and 0.5 wt % copper.

Example 7

The catalyst of Example 6 was tested as a catalyst for the dehydrogenation of ethane using the apparatus of FIG. 1. A quartz reactor 12 was employed. The performance of this catalyst was compared to that of three other catalysts: one having Pd, as the only metal component, a second comprising only Pt, and a third catalyst comprising Pt and Cu. The reaction conditions are summarised in Table 5. The ethane conversions and selectivities obtained are summarised in Table 6.

TABLE 5

|  | 1 wt % Pd/ 0.5 wt % Cu | Pd only | Pt only | Pt/Cu |
|---|---|---|---|---|
| GHSV @ stp (/h) | 120864 | 120482 | 121073 | 119948 |
| ethane flow (g/min) | 18.94 | 18.07 | 18.94 | 18.07 |
| hdrogen flow (g/min) | 1.14 | 1.18 | 1.14 | 1.18 |
| Oxygen flow (g/min) | 9.09 | 9.39 | 9.09 | 9.39 |
| nitrogen flow (g/min) | 4.95 | 4.80 | 5.00 | 4.60 |

TABLE 6

|  | 1 wt % Pd/ 0.5 wt % Cu | Pd only | Pt only | Pt/Cu |
|---|---|---|---|---|
| target (nominal) loadings Pt/Pd/Cu (wt %) | —/1.0/0.5 | —/0.2/— | 1.0/—/— | 1.0/—/0.5 |
| ethane conversion (%) | 78.17 | 76.29 | 73.55 | 78.00 |
| ethylene selectivity (g per 100 g ethane converted) | 72.01 | 69.70 | 71.44 | 71.47 |

Example 8

Preparation of Pd/Ge Catalysts

In this example, Pd/Ge catalysts having the following Pd:Ge atomic ratios were prepared: 1:5.8, 1:1 and 2:1. The nominal Pd:Ge weight % ratios of these catalysts were 1:4, 1:0.74 and 1:0.37, respectively.

The catalysts were prepared by sequential impregnation of 30 ppi ceramic foam blocks (lithium aluminium silicate with alumina washcoat, pre-calcined in air to 1200° C.,) with aqueous tetramminepalladium(II) chloride and germanium tetrachloride in ethanol. The foam blocks employed were 15 mm in diameter and 30 mm in depth. Between impregnations, the blocks were dried in air at 120–140° C. for ca. 30 minutes, calcined in air at 450° C. for 30 minutes, and then cooled to room temperature. Once all the impregnation solution had been absorbed onto the foam the blocks were calcined in air at 600° C. for 6 hours.

Prior to ATC testing the catalysts were given an in situ reduction at 750° C. under flowing hydrogen (ca. 1.0 nl/min) and nitrogen (ca. 1.5 nl/min) for 1 hour.

Example 9

The catalysts of Example 8, and Comparative Example A were tested as catalysts for the oxidative dehydrogenation of ethane. Each catalyst was mounted in the apparatus of FIG.

1, and an oxidative dehydrogenation reaction was carried out under the conditions summarised in Table 7 below.

TABLE 7

|  | Pd/Ge (atomic ratio Pd:Ge = 1:5.8) | Pd/Ge (atomic ratio Pd:Ge = 1:1) | Pd/Ge (atomic ratio Pd:Ge = 2:1) | A (Pt only) |
| --- | --- | --- | --- | --- |
| GHSV @ stp/h | 250972 | 250734 | 250719 | 250510 |
| ethane flow (g/min) | 8.07 | 8.07 | 8.07 | 8.07 |
| hydrogen flow (g/min) | 7.87 | 7.87 | 7.87 | 7.87 |
| Oxygen flow (g/min) | 3.94 | 3.94 | 3.94 | 3.94 |
| nitrogen flow (g/min) | 2.30 | 2.27 | 2.27 | 2.25 |

As shown in Table 8 below, the ethylene selectivities of the catalysts of Example 8 were greater than that of Comparative Example A.

TABLE 6

|  | Pd/Ge (atomic ratio Pd:Ge = 1:5.8) | Pd/Ge (atomic ratio Pd:Ge = 1:1) | Pd/Ge (atomic ratio Pd:Ge = 2:1) | A (Pt only) |
| --- | --- | --- | --- | --- |
| ethane conversion (%) | 76.35 | 76.74 | 78.83 | 78.27 |
| selectivity (g ethylene per 100 g ethane converted) | 70.05 | 70.10 | 69.25 | 68.57 |

Example 10

Preparation of Pd/In Catalysts

In this Example, a Pd/In catalyst having a Pd:In atomic ratio of 1:1 was prepared.

Foam blocks (lithium aluminium silicate (LAS) with an alumina wash-coat (28 mm diameter by 30 mm deep, 30 pores per inch) were pre-calcined in air at 1200° C. to remove porosity/surface area associated with the wash-coat. The blocks were then repeatedly impregnated from an aqueous solution of tetra-amine palladium(II) chloride nitrate and indium(III) nitrate with sufficient salt to give a nominal loading of 2 wt % palladium and 2.16 wt % indium, assuming 100% absorption of the salt onto the foam. (Corresponding to an atomic palladium:indium ratio of 1:1). Impregnation was carried out alternately from the Pd and In solutions Between impregnations excess solution was removed from the foam blocks and the blocks were dried in air at 120–140° C. then calcined in air at 450° C. for ca. 30 minutes.

Once all the solutions had been absorbed onto the foams the blocks were dried and given a final air calcination at 600° C. for 6 hours.

Example 11

The catalyst of Example 10 was loaded into the quartz reactor then given an in-situ hydrogen reduction at 750° C. for 1 hour.

The catalyst was then tested as a catalyst for the oxidative dehydrogenation of ethane. The catalyst was mounted in the apparatus of FIG. 1, and an auto-thermal cracking reaction was carried out under the conditions summarized in Table 9 below.

TABLE 9

| GHSV @ stp/h | 119845 |
| --- | --- |
| Ethane flow (g/min) | 18.07 |
| Hydrogen flow (g/min) | 1.18 |
| Oxygen flow (g/min) | 9.39 |
| Nitrogen flow(g/min) | 4.56 |

Table 10 below shows the ethane conversion and ethylene selectivity of the reaction.

TABLE 10

| Ethane conversion (%) | 80.01 |
| --- | --- |
| Ethylene selectivity (g ethylene per 100 g ethane converted) | 71.37 |

The invention claimed is:

1. A process for the production of an olefin from a hydrocarbon by autothermal cracking, which process comprises:
partially combusting the hydrocarbon and an oxygen-containing gas in the presence of a catalyst, wherein the stoichiometric ratio of hydrocarbon to oxygen is 5 to 16 times the stoichiometric ratio of hydrocarbon to oxygen required for complete combustion of the hydrocarbon to carbon dioxide and water, wherein the catalyst comprises palladium and at least one further metal selected from the group consisting of In, Sn, and Cu.

2. A process as claimed in claim 1, wherein said partial combustion of hydrocarbon and oxygen-containing gas is carried out in the presence of hydrogen.

3. A process as claimed in claim 1, wherein said catalyst further comprises alkali metal ions.

4. A process as claimed in claim 1, wherein said hydrocarbon comprises at least one hydrocarbon selected from the group consisting of ethane, propane and butane.

5. A process as claimed in claim 1, in which the catalyst comprises Pd, Pt and Cu.

6. A process as claimed in claim 1, in which the catalyst comprises Pd, Pt and Sn.

* * * * *